(12) United States Patent
Casey et al.

(10) Patent No.: US 10,646,244 B2
(45) Date of Patent: *May 12, 2020

(54) SURGICAL TOOL WITH SHEATH

(71) Applicant: GYRUS ACMI, INC., Southborough, MA (US)

(72) Inventors: Jay A. Casey, Memphis, TN (US); Kevin C. Edwards, Olive Branch, MS (US)

(73) Assignee: GYRUS ACMI, INC., Southborough, MA (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/054,942

(22) Filed: Feb. 26, 2016

(65) Prior Publication Data

US 2016/0174999 A1    Jun. 23, 2016

Related U.S. Application Data

(63) Continuation of application No. 12/938,786, filed on Nov. 3, 2010, now Pat. No. 9,308,013.

(51) Int. Cl.
*A61B 17/32* (2006.01)
*A61B 17/16* (2006.01)
(Continued)

(52) U.S. Cl.
CPC .... *A61B 17/32002* (2013.01); *A61B 17/1622* (2013.01); *A61B 17/1631* (2013.01);
(Continued)

(58) Field of Classification Search
CPC ........ A61B 17/320016; A61B 17/1631; A61B 2017/320024; A61B 2017/320028;
(Continued)

(56) References Cited

U.S. PATENT DOCUMENTS 3,844,272 A   10/1974   Banko
4,646,738 A    3/1987   Troll
(Continued)

FOREIGN PATENT DOCUMENTS

WO   1998/049953 A1   11/1998
WO     99/15237 A1    4/1999

OTHER PUBLICATIONS

Sep. 19, 2017 Office Action issued in Chinese Application No. 201610136223.X.
(Continued)

*Primary Examiner* — Tan-Uyen T Ho
*Assistant Examiner* — Chima U Igboko
(74) *Attorney, Agent, or Firm* — Oliff PLC

(57) ABSTRACT

A surgical tool can include a main unit and a first rigid sheath. The main unit includes an inner tube that is received within an outer tube. The first rigid sheath removably receives the main unit and connects to the main unit via a coupling between a first connector portion of the main unit and a second connector portion of the rigid sheath. The first rigid sheath can be completely removed from the main unit when the first connector portion is decoupled from the second connector portion. A different rigid sheath having a different shape from the shape of the first rigid sheath can then be removably attached to the main unit instead of the first rigid sheath. A surgical tool kit includes a plurality of rigid sheaths having different shapes and having the ability to be removably attached to the main unit.

28 Claims, 11 Drawing Sheets

(51) Int. Cl.
*A61B 17/00* (2006.01)
*A61B 17/29* (2006.01)

(52) U.S. Cl.
CPC ...... *A61B 17/1633* (2013.01); *A61B 17/1615* (2013.01); *A61B 2017/0046* (2013.01); *A61B 2017/00464* (2013.01); *A61B 2017/00477* (2013.01); *A61B 2017/00973* (2013.01); *A61B 2017/2904* (2013.01); *A61B 2017/320032* (2013.01)

(58) Field of Classification Search
CPC ......... A61B 2017/320032; A61B 2017/32004; A61B 2017/0046; A61B 2017/00464; A61B 2017/2901; A61B 2017/2904; A61B 2017/2905; A61B 10/02; A61B 10/0233; A61B 10/0266; A61B 10/04; A61B 10/06; A61B 2010/0208; A61B 2010/0225; A61B 2017/00477; A61B 2017/00486; A61B 2017/320052; A61B 2017/347; A61B 17/32; A61B 17/32002; A61B 17/3205; A61B 17/320783
See application file for complete search history.

(56) References Cited

U.S. PATENT DOCUMENTS

| | | | |
|---|---|---|---|
| 4,674,500 A | | 6/1987 | DeSatnick |
| 5,192,292 A | | 3/1993 | Cezana et al. |
| 5,282,821 A | | 2/1994 | Donahue |
| 5,320,635 A | | 6/1994 | Smith |
| 5,346,502 A | * | 9/1994 | Estabrook ...... A61B 17/320068 601/2 |
| 5,364,395 A | | 11/1994 | West, Jr. |
| 5,529,580 A | * | 6/1996 | Kusunoki ........ A61B 17/32002 604/22 |
| 5,601,583 A | | 2/1997 | Donahue et al. |
| 5,741,084 A | | 4/1998 | Del Rio et al. |
| 5,741,286 A | | 4/1998 | Recuset |
| 5,741,287 A | | 4/1998 | Alden et al. |
| 5,810,809 A | | 9/1998 | Rydell |
| 5,833,692 A | * | 11/1998 | Cesarini ........... A61B 17/32002 606/79 |
| 5,911,701 A | | 6/1999 | Miller et al. |
| 5,922,003 A | | 7/1999 | Anctil et al. |
| 5,924,206 A | | 7/1999 | Cote et al. |
| 5,989,275 A | | 11/1999 | Estabrook et al. |
| 6,024,749 A | | 2/2000 | Shturman et al. |
| 6,206,844 B1 | | 3/2001 | Reichel et al. |
| 6,221,088 B1 | | 4/2001 | Bays |
| 6,464,711 B1 | | 10/2002 | Emans et al. |
| 6,533,749 B1 | | 3/2003 | Mitusina et al. |
| 6,976,969 B2 | | 12/2005 | Messerly |
| 7,276,074 B2 | | 10/2007 | Adams et al. |
| 7,455,679 B2 | | 11/2008 | Adams et al. |
| 8,313,489 B2 | | 11/2012 | Adams et al. |
| 8,475,482 B2 | | 7/2013 | Palmer et al. |
| 8,968,210 B2 | | 3/2015 | Mugan et al. |
| 2003/0181934 A1 | | 9/2003 | Johnston et al. |
| 2004/0059363 A1 | * | 3/2004 | Alvarez ........... A61B 17/32002 606/170 |
| 2004/0181250 A1 | * | 9/2004 | Adams ............. A61B 17/32002 606/170 |
| 2005/0054972 A1 | | 3/2005 | Adams et al. |
| 2005/0277970 A1 | * | 12/2005 | Norman ........... A61B 17/32002 606/180 |
| 2006/0025793 A1 | | 2/2006 | Gibson et al. |
| 2006/0089628 A1 | | 4/2006 | Whitman |
| 2006/0122640 A1 | | 6/2006 | Gordon et al. |
| 2006/0264927 A1 | | 11/2006 | Ryan |
| 2007/0010738 A1 | | 1/2007 | Mark et al. |
| 2007/0162062 A1 | | 7/2007 | Norton et al. |
| 2007/0270751 A1 | * | 11/2007 | Stangenes ........ A61B 17/00234 604/164.1 |
| 2008/0021278 A1 | | 1/2008 | Leonard et al. |
| 2008/0172051 A1 | | 7/2008 | Masuda et al. |
| 2008/0188848 A1 | | 8/2008 | Deutmeyer et al. |
| 2008/0234708 A1 | | 9/2008 | Houser et al. |
| 2008/0234711 A1 | | 9/2008 | Houser et al. |
| 2009/0036911 A1 | | 2/2009 | Stulen |
| 2010/0063513 A1 | | 3/2010 | Braga et al. |
| 2010/0087711 A1 | | 4/2010 | Edwards |

OTHER PUBLICATIONS

Apr. 4, 2016 Office Action issued in Australian Patent Application No. 2015204335.
Oct. 28, 2014 Office Action issued in Australian Application No. 2011323989.
Nov. 28, 2012 Search Report (with Written Opinion) issued in International Patent Application No. PCT/US2011/054562.
May 8, 2013 International Preliminary Report on Patentability issued in International Patent Application No. PCT/US2011/054562.
Sep. 9, 2014 Office Action issued in Japanese Patent Application No. 2013-537675.
Jan. 29, 2014 Restriction/Election of Species Requirement issued in U.S. Appl. No. 12/938,786.
May 8, 2014 Office Action issued in U.S. Appl. No. 12/938,786.
Dec. 4, 2014 Office Action issued in U.S. Appl. No. 12/938,786.
May 21, 2015 Office Action issued in U.S. Appl. No. 12/938,786.
Dec. 31, 2015 Notice of Allowance issued in U.S. Appl. No. 12/938,786.
Jul. 12, 2016 Office Action issued in Japanese Patent Application No. 2015-127785.
Feb. 5, 2018 Office Action issued in European Application No. 11 773 602.5.
Jul. 2, 2019 Office Action issued in European Application No. 11 773 602.5.

* cited by examiner

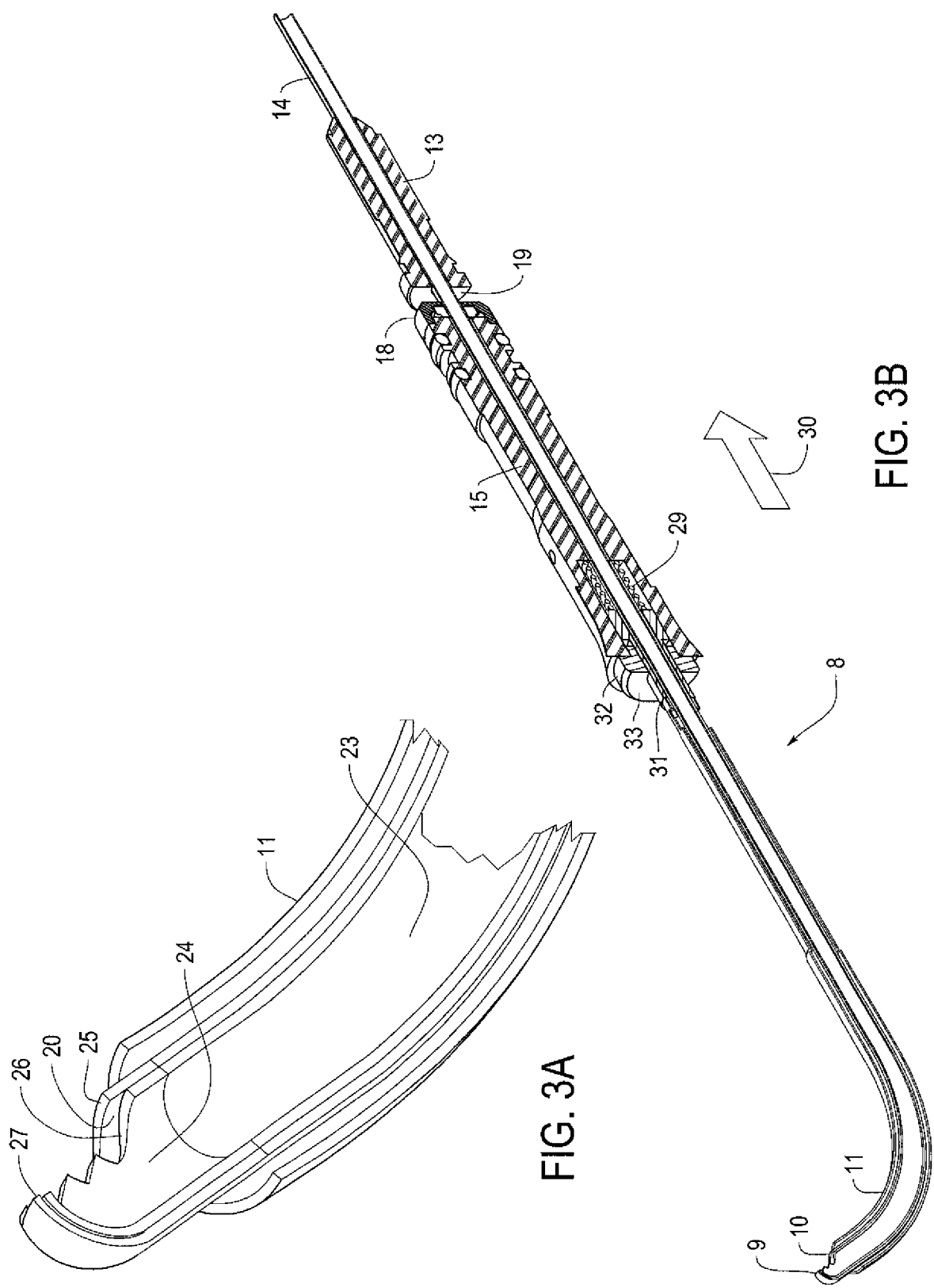

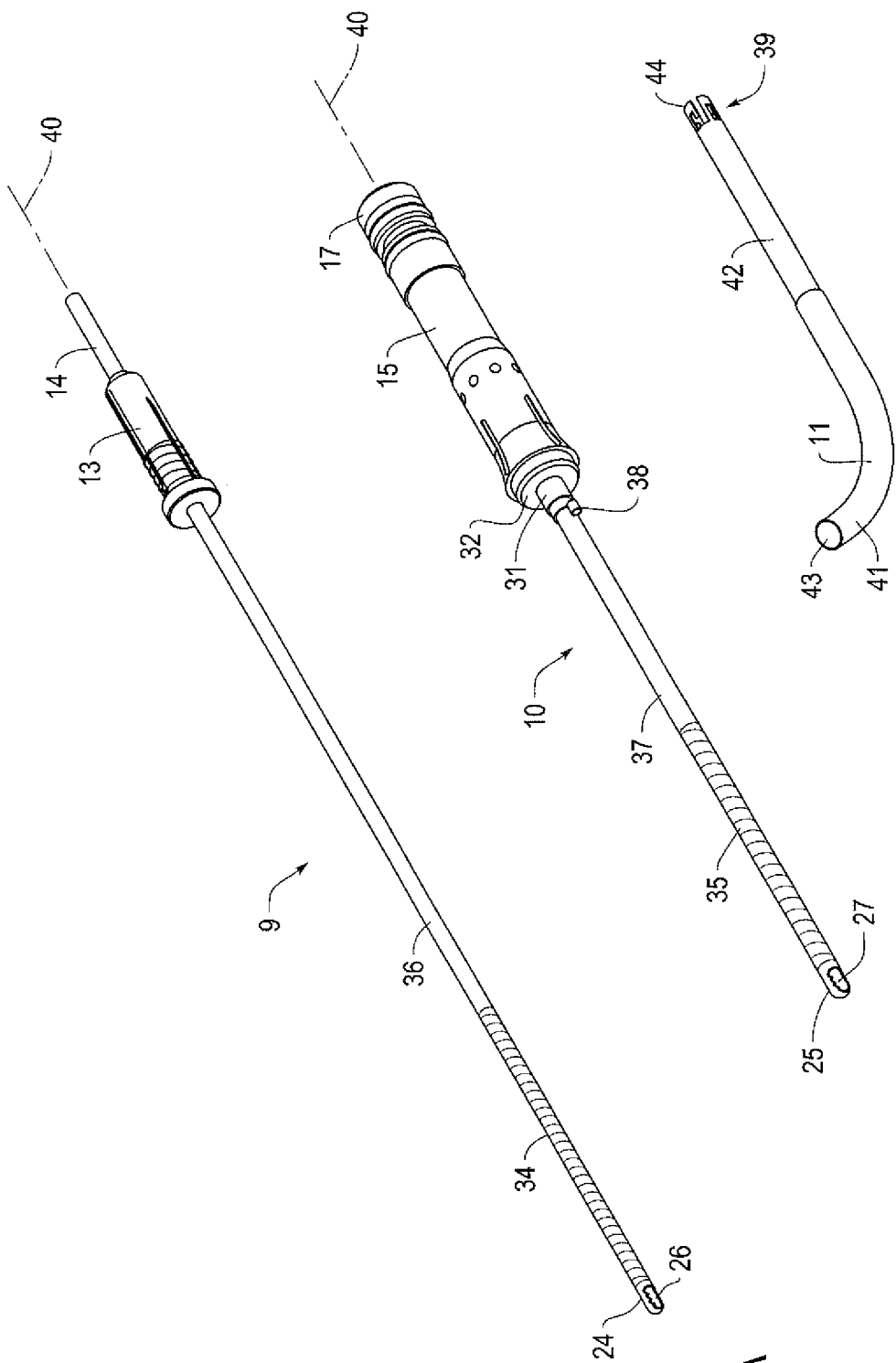

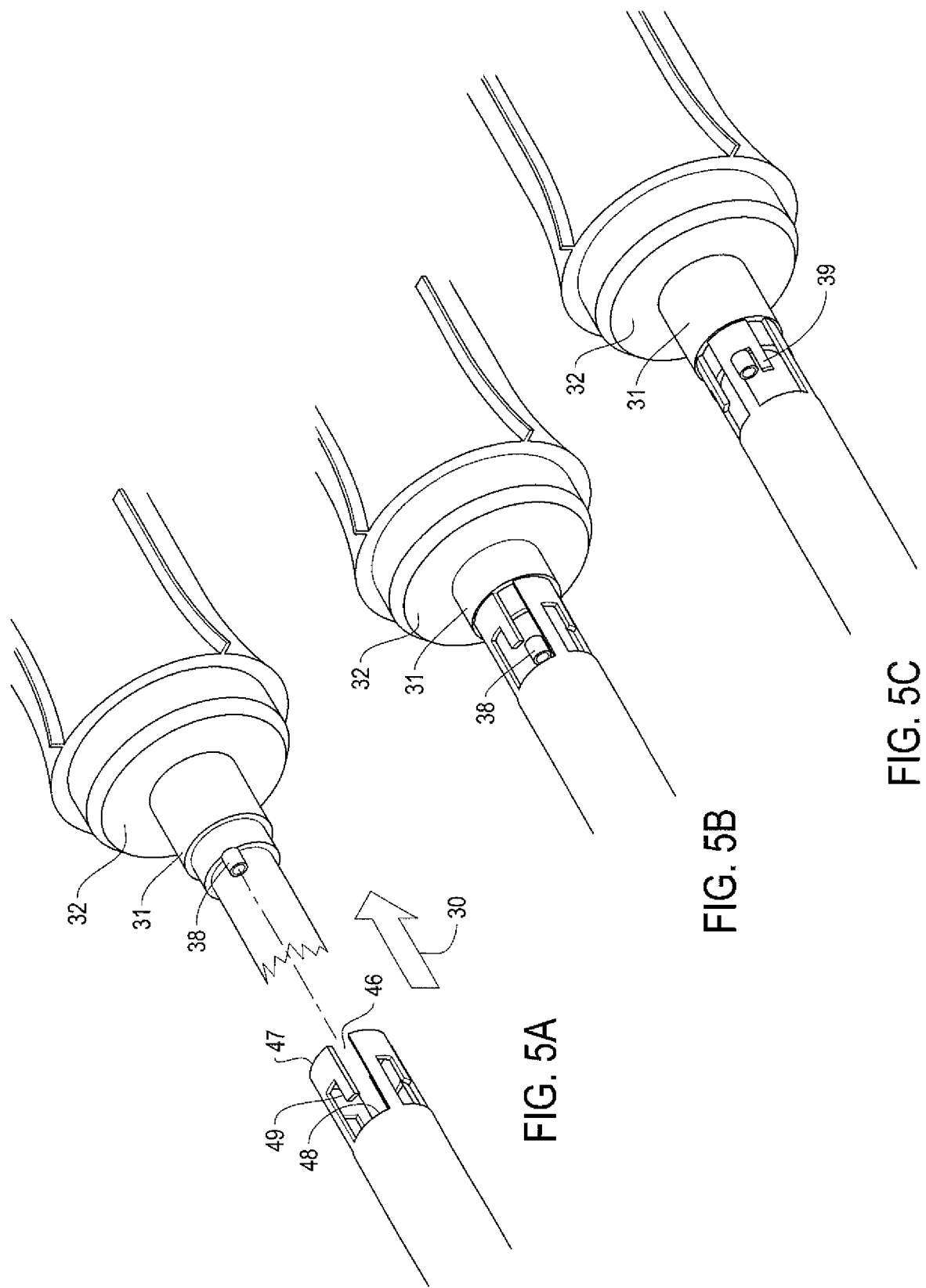

SURGICAL TOOL WITH SHEATH

This is a Continuation of application Ser. No. 12/938,786 filed Nov. 3, 2010. The disclosure of the prior application is hereby incorporated by reference herein in its entirety.

BACKGROUND

This disclosure relates to improved surgical tools, methods of performing surgical procedures with a surgical tool assembly, and to surgical tool kits. In particular, the disclosure relates to such surgical tool assemblies usable to shave, cut, resect, abrade and/or remove tissue, bone and or other bodily materials using rigid sheaths having different shapes.

Surgical apparatus used to shave, cut, resect, abrade and/or remove tissue, bone and or other bodily materials are known. Such surgical apparatus can include a cutting surface, such as a rotating blade, disposed on an elongated inner tube that is rotated within an elongated outer tube having a cutting window. The inner and outer tubes together forming a surgical cutting blade. In general, the elongated outer tube includes a distal end defining an opening or cutting window that exposes the cutting surface of the inner tube (at the distal end of the inner tube) to tissue, bone and/or any other bodily materials. A powered handpiece is used to rotate the inner tube with respect to the outer tube while an outer tube hub (connected to the proximal end of the outer tube) is rigidly fixed to the handpiece and an inner tube hub (connected to the proximal end of the inner tube) is loosely held in place by the powered handpiece and can move axially.

During surgery, it may be necessary or helpful to precisely orient a tip of the surgical cutting blade (defining the cutting surface within the cutting window) at a specific angle. Because of this requirement, it is known to provide multiple surgical cutting blades having first ends angled to different fixed degrees. Thus, depending on the needs or requirements of the surgery, a surgeon can switch between multiple different surgical cutting blades multiple times during surgery so as to precisely orient the selected surgical cutting blade in the exact location he/she is trying to reach.

A number of difficulties have been encountered in attempting to develop reliable flexible-shaft surgical blades that would allow the surgeon to use only one surgical cutting blade, as opposed to changing between different surgical cutting blades having different shapes and/or window orientations based on a newly desired target orientation. For example, surgical cutting blades have been developed that are initially straight and can then be bent to a desired angle. However, the drawback for this design is that once the surgical cutting blade instrument is bent, any rebend of the surgical cutting blade instrument to obtain a different angled configuration is not effective or reliable in allowing for proper rotation of the inner tube. Instead, a new surgical cutting blade must be used if a different angle configuration of the blade is required/desired. Another example involves the use of a lever arm that allows a surgeon to bend the surgical cutting blade instrument to a specific angle and hold the instrument at that angle. However, the drawback for this design is that the lever cannot be locked into place and thus requires the surgeon to continuously apply pressure to the lever in order to hold the instrument in the desired angled orientation. Additionally, typically, the bending of the instrument using the lever is limited to only one direction (typically concave) and is not bi-directional.

SUMMARY

User preferences, such as those of the surgeons, as well as the demands of surgery dictate limitless requirements for the curvature of a surgical tool and for the orientation of the cutting window of the tool. Accommodating such user preferences and surgery requirements during surgical procedures requires the use of many surgical tools having different angled configurations and/or window orientations. The use of multiple surgical tools can be very costly and requires hospitals/surgeons to come equipped with a large variety of surgical tools so as to accommodate any and all needs that arise during surgery.

It would be advantageous to provide an arrangement that would allow the surgeon to utilize one surgical cutting tool (or blade) for all surgery requirements. A flexible cutting blade is provided that is selectively connectable to a plurality of rigid sheaths having different shapes. The arrangement allows the surgeon to use one blade for many surgical applications (because the blade can be coupled with a sheath having any desired shape) without having the need to purchase, store and use large quantities of blade inventory to meet the demands of surgery.

In various exemplary embodiments, a main unit may be provided that allows for the attachment of a rigid sheath. The rigid sheath may advantageously be formed in a straight or angled configuration such that insertion of the main unit into the rigid sheath conforms the main unit to the configuration of the sheath. The main unit allows for such conformation via flexible portions of its inner and outer tubes. These flexible portions conform to any bend of the rigid sheath and thus allow the surgeon to use one main unit at different angles (or in a straight configuration) by attaching different angled sheaths. A first connector portion is located on the main unit and a second connector portion is located on the rigid sheath that allow for the coupling between the main unit and the rigid sheath.

In accordance with one aspect of the invention, a surgical tool may include a main unit having inner and outer tubes, each having first and second ends. The inner tube may include a cutting surface at the first end and a flexible portion located between the first end and the second end. The outer tube may include a cutting window at the first end and a flexible portion located between the first end and the second end. The inner tube is received within the outer tube so as to align the cutting surface of the inner tube with the cutting window of the outer tube. The surgical tool may also include a rigid sheath having a first end and a second end such that the rigid sheath removably receives the main unit allowing the cutting window to extend beyond an opening of the first end of the rigid sheath. The surgical tool further includes a connector having a first connector portion located on the main unit and a second connector portion located on the rigid sheath. The first connector portion, when connected to the second connector portion, detachably couples the rigid sheath to the main unit. The main unit can be completely removed from the rigid sheath when the first and second connector portions are uncoupled from each other.

In some embodiments, the rigid sheath includes a first tapered portion extending from the first end of the rigid sheath for a first tapered distance along the rigid sheath. In some embodiments, the rigid sheath includes a second tapered portion extending from the second end of the rigid sheath for a second tapered distance along the rigid sheath. Additionally, in some embodiments, a rigid sheath includes an untapered portion extending between the first tapered portion and the second tapered portion, the untapered portion having a larger diameter than the first and second tapered portions.

In some embodiments, the flexible portion of the inner tube and the flexible portion of the outer tube are radially, symmetrically bendable about a longitudinal, central axis of the surgical tool.

In some embodiments, the rigid sheath is straight along its entire length.

In some embodiments, the rigid sheath includes a curved portion at least near the first end of the rigid sheath. In some embodiments, for example, an angle of the curved portion can be one of 15°, 30°, 40°, 60°, 75°, and 110°; however, other angles of the curved portion are possible.

In some embodiments, the flexible portion of the inner and outer tubes assumes a substantially straight orientation when the main unit is not inserted into the rigid sheath.

In some embodiments, the first and second connector portions are adjustably connectable to each other such that an orientation of the cutting window relative to a longitudinal axis of the rigid sheath can be radially adjusted.

In some embodiments, one of the first and second connector portions includes a plurality of individually selectable engagement members, and the other of the first and second connector portions includes an engaging member that is selectively engaged with one of the engagement members to select a desired orientation of the cutting window.

In some embodiments, for example, there are four of the engagement members to provide for selectable orientation of the cutting window.

In some embodiments, for example, the four selectable orientations are provided at intervals of 90° about the longitudinal axis of the surgical tool. In some embodiments, the engagement members are provided on the rigid sheath and the engaging member is provided on the main unit.

In some embodiments, the engaging member is a protruding key, and the engagement members are a plurality of slots.

In some embodiments, the first connector portion is provided on the outer tube.

In some embodiments, the flexible portion of the inner tube is located at least near the first end of the inner tube, and the flexible portion of the outer tube is located at least near the first end of the outer tube.

In some embodiments, the outer tube of the main unit cannot rotate relative to the rigid sheath when the first and second connector portions are coupled to each other.

In accordance with one aspect of the invention, a method of performing a surgical procedure with a surgical tool assembly includes inserting a surgical tool into a passage of a patient. The surgical tool includes a main unit and a first rigid sheath. The main unit includes inner and outer tubes having first and second ends. The inner tube includes a cutting surface at the first end and a flexible portion located between the first end and the second end. The outer tube includes a cutting window at the first end and a flexible portion located between the first end and the second end. The inner tube is received within the outer tube so as to align the cutting surface of the inner tube with the cutting window of the outer tube. The first rigid sheath is disposed over the main unit and has a first end and a second end. The cutting window extends beyond an opening of the first end of the first rigid sheath. The method of performing a surgical procedure with a surgical tool assembly further includes removing the surgical tool from the passage of the patient. Next, the method includes completely removing the main unit from the first rigid sheath and inserting the main unit into a second rigid sheath. The second rigid sheath has a first end and a second end and has a shape that is different from a shape of the first rigid sheath. Finally, the method of performing a surgical procedure with a surgical tool assembly further includes inserting the surgical tool comprised of the main unit and the second rigid sheath into the passage of the patient.

In some embodiments, the first rigid sheath is straight and the second rigid sheath has a curved portion near its first end.

In some embodiments, the first and second rigid sheaths each have curved portions near their first ends. The curved portion of the first rigid sheath has an angle of curvature that is different from an angle of curvature of the curved portion of the second rigid sheath.

In some embodiments, the method of performing a surgical procedure with a surgical tool assembly further includes respectively coupling the first and second rigid sheaths to the main unit to adjust a radial orientation of the cutting window relative to a longitudinal axis of the rigid sheath.

In accordance with another aspect of the invention, a surgical tool kit includes a main unit, a first rigid sheath and at least one additional rigid sheath. The main unit includes inner and outer tubes having first and second ends. The inner tube includes a cutting surface at the first end and a flexible portion located between the first end and the second end. The outer tube includes a cutting window at the first end and a flexible portion located between the first end and the second end. The inner tube is received within the outer tube so as to align the cutting surface of the inner tube with the cutting window of the outer tube. The first rigid sheath has a first end and a second end and is removably attachable to the main unit such that the cutting window extends beyond an opening of the first end of the first rigid sheath. The at least one additional rigid sheath has a first end and a second end and is removably attachable to the main unit instead of the first rigid sheath such that the cutting window extends beyond an opening of the first end of the at least one additional rigid sheath. The at least one additional rigid sheath has a shape that is different from a shape of the first rigid sheath.

In some embodiments, the first rigid sheath is straight and the at least one additional rigid sheath has a curved portion at least near the first end thereof.

In some embodiments, the kit further includes a plurality of the additional rigid sheaths, each having a differently-curved curved portion.

In some embodiments, the kit further includes a plurality of the additional rigid sheaths, each having a shape that is different from each other and from the shape of the first rigid sheath.

BRIEF DESCRIPTION OF THE DRAWINGS

Various exemplary embodiments of the disclosed surgical tool will be described in detail with reference to the following drawings in which:

FIG. 3B is a cross-sectional view of the surgical tool of FIG. 2, and FIG. 3A is an enlarged view of the curved end of the surgical tool of FIG. 3;

FIGS. 4A-C are simplified, perspective views of the inner tube, outer tube and rigid sheath, separated from any connection with each other;

FIGS. 5A-C are enlarged, perspective views of the outer tube disconnected from and connected to the rigid sheath, respectively;

DETAILED DESCRIPTION OF EMBODIMENTS

The following exemplary embodiments are described below with reference to the figures in the context of human surgery, such as ear, nose and throat surgery, and in particular sinus surgery as well as head and neck surgery. The following exemplary embodiments may also be utilized in spinal surgery, orthopedic surgery, and various other surgical applications. All exemplary embodiments of the invention are intended to be used in any applicable field of endeavor.

Figure 1:
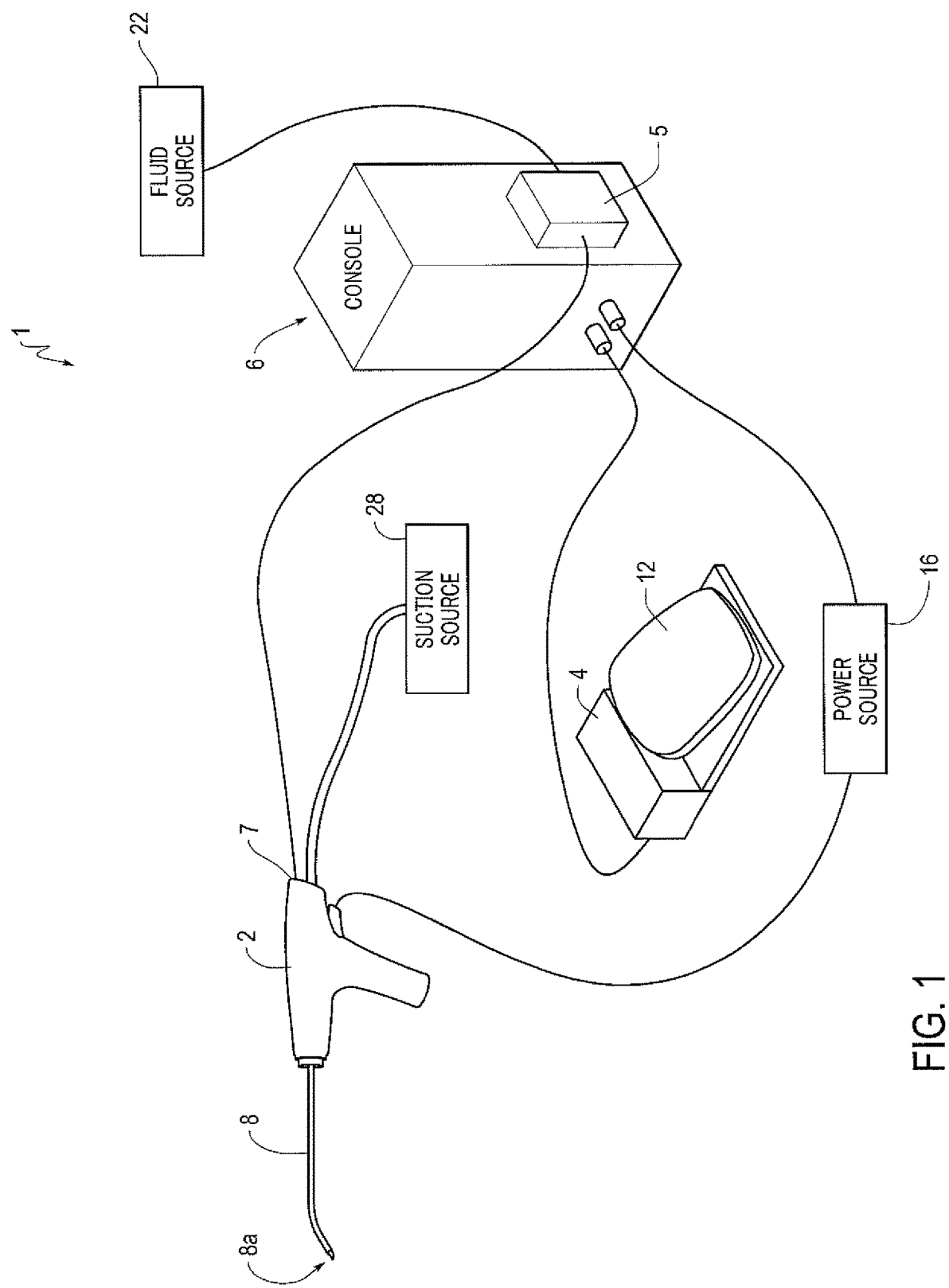
FIG. 1 illustrates a perspective view of a powered surgical tool system that incorporates a controller, power source, fluid source and suction source.

FIG. 1 is a schematic of a powered surgical tool system. Except for the cutting tool, to be described hereafter, the system may be in accordance with the system disclosed in U.S. Pat. No. 7,247,161, the disclosure of which is incorporated herein by reference in its entirety. As shown in FIG. 1, the powered surgical tool system 1 includes a handle 2, a footswitch 4 (with pedal 12), power source 16, fluid (liquid and/or gas) source 22, suction source 28, a controller 6, console 3, fluid pump 5 and a fluid inlet/irrigation outlet 7. The handle 2 is connected, at its distal end, to a surgical tool 8. The surgical tool 8 includes a cutting instrument 8a at its distal end that is used to cut, shave, remove, resect and/or abrade tissue, bone and/or other bodily materials.

Figure 2:
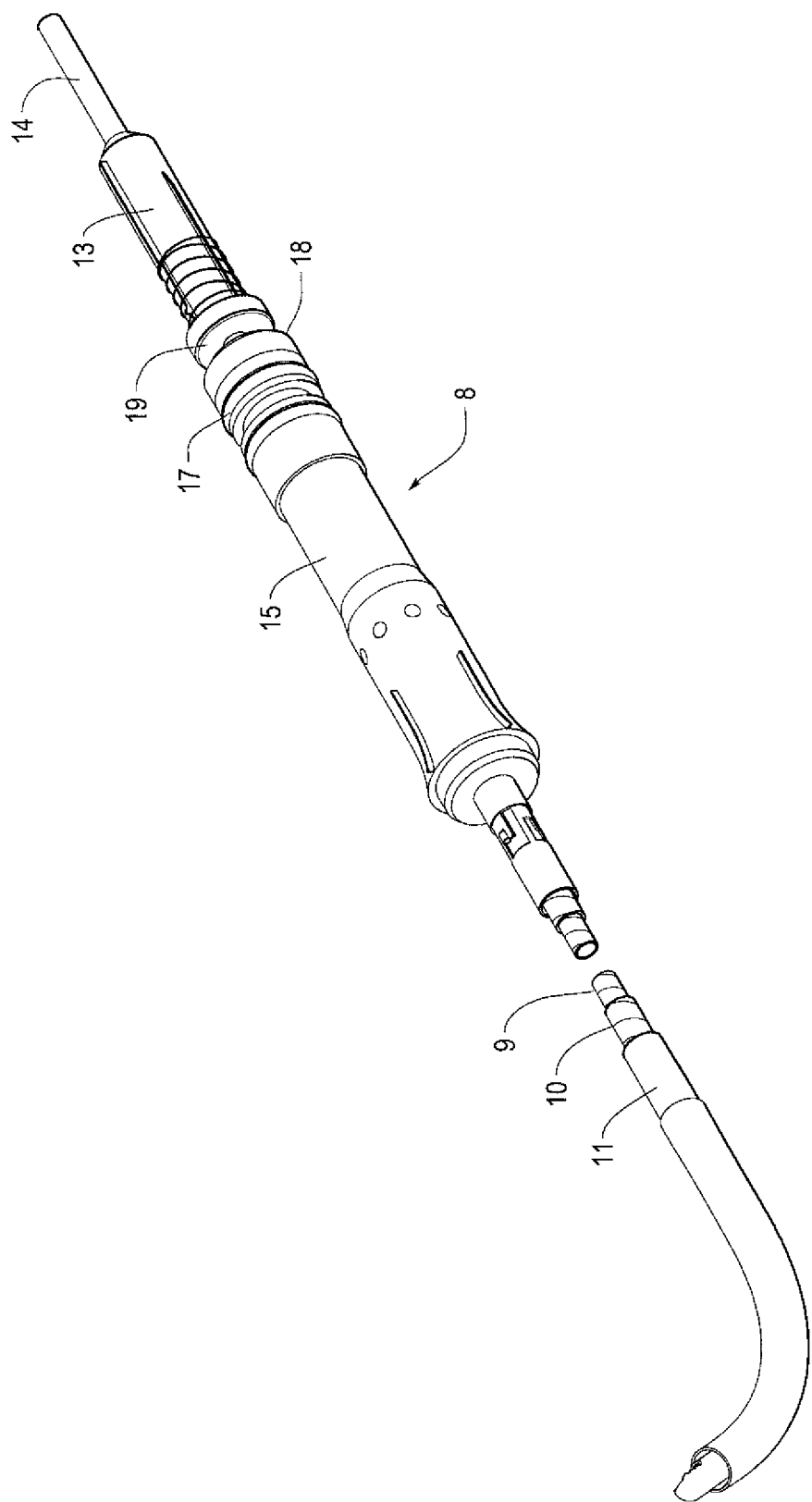
FIG. 2 is a perspective view of an exemplary embodiment of the main unit in accordance with the present disclosure.

FIG. 2 illustrates a perspective view of an exemplary embodiment of the surgical tool 8, in accordance with aspects of the invention. The tool 8 incorporates an inner tube 9, an outer tube 10 and a rigid sheath 11. In this exemplary embodiment, an inner tube hub 13 is formed on the second end 14 of the inner tube 9 and an outer tube hub 15 is formed on the second end 17 of the outer tube 10. The inner tube 9 is inserted into a fluid passage 20 (FIG. 3A) formed within the outer tube 10 so that the inner tube 9 is co-axially disposed within the outer tube 10 until the top portion 19 of the inner tube hub 13 contacts or nearly contacts the bottom portion 18 of the outer tube hub 15. The outer tube 10 has a larger diameter than the inner tube 9, thus allowing for insertion of the inner tube 9 within the outer tube 10. However, it should be appreciated that the inner and outer tubes will be pre-assembled prior to delivery to the customer. Thus, a customer will most likely not be inserting the inner tube into the outer tube. Instead, the customer will merely be attaching and detaching the rigid sheath from the main unit.

Figure 12:
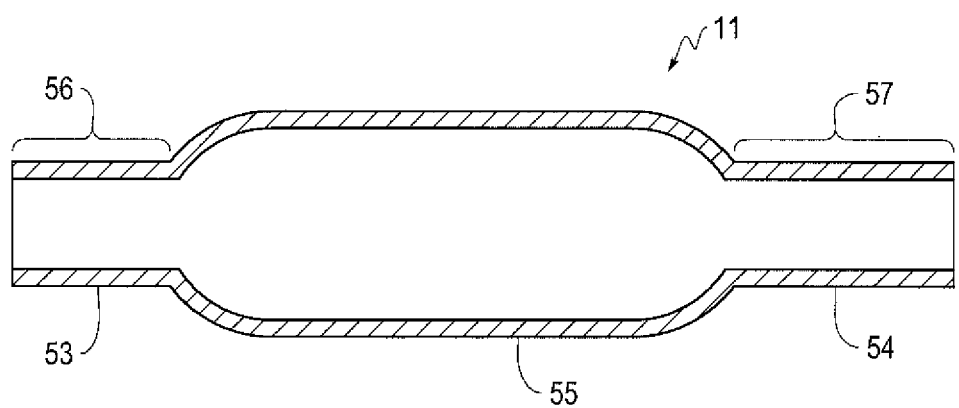
FIG. 12 is a cross-sectional view of an exemplary embodiment of the rigid sheath.

FIG. 12 illustrates a cross-sectional view of the rigid sheath 11. In this exemplary embodiment, the rigid sheath 11 includes a first tapered portion 53, a second tapered portion 54, and an untapered portion 55. The first tapered portion 53 extends from the first end 41 of the rigid sheath 11 for a first tapered distance 56 along the rigid sheath 11. The second tapered portion 54 extends from the second end 42 of the rigid sheath 11 for a second tapered distance 57 along the rigid sheath 11. The untapered portion 55 extends between the first tapered portion 53 and the second tapered portion 54. The untapered portion has a larger diameter than the first tapered portion 53 and second tapered portion 54. The larger diameter of the portion 55 makes it easier to push the main unit (tubes 9 and 10) through the sheath 11, especially when the sheath 11 includes one or more curves. The tapered portions 53, 54 help prevent vibration between the rigid sheath 11 and the tubes (inner 9 and outer 10). The diameter of the larger-diameter untapered portion 55 depends on a length of the rigid cutting portion at the distal end of the outer tube 10. However, in a straight rigid sheath 11, for example, the entire rigid sheath 11 may include only a small diameter like the tapered portions 53 and 54.

Figure 7:
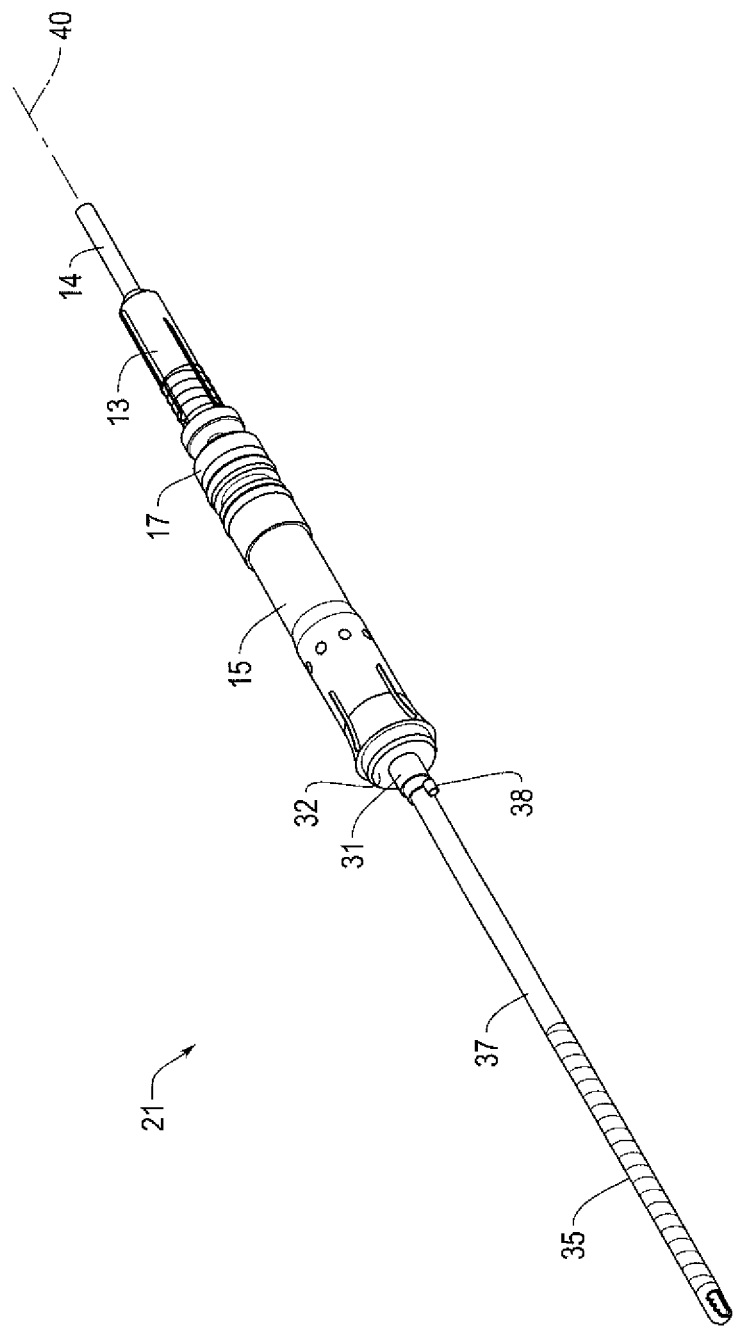
FIG. 7 is a perspective view of the orientation of the surgical tool when the inner tube is disposed in the outer tube only (no rigid sheath is provided)

The inner tube 9, inner tube hub 13, outer tube 10 and outer tube hub 15 form a main unit 21 (FIG. 7). The inner and outer tube hubs 13, 15 couple the inner and outer tubes 9, 10, respectively, to the handle 2 such that the inner and outer tubes 9, 10 are rotatable relative to one another and the handle 2.

FIG. 3 illustrates a cross-sectional view of the surgical tool 8 with the inner tube 9 co-axially disposed within the fluid passage 20 of the outer tube 10. FIG. 3A is an enlarged view of the distal end of the tool. The inner tube 9 includes a fluid/bodily materials removal passage 23 that extends the length of the inner tube 9. The inner tube 9 also includes a cutting surface 26 at its first end 24 while the outer tube includes a cutting window 27 at its first end 25. The inner tube 9 is co-axially disposed within the outer tube 10 such that the cutting surface 26 is exposed at the cutting window 27. The cutting surface 26 disposed within the cutting window 27 form a cutting instrument 8a, which cuts by rotating the inner tube 9 within the outer tube 10.

In an exemplary embodiment, for example, a spring 29 is disposed on the interior of the outer tube hub 15 and on the exterior of the outer tube 10. The spring 29 allows for movement of a compliance portion 31 of the outer tube 10. The compliance portion 31 is disposed around the circumference of the outer tube 10 and fixed thereto. When pressure is applied to the compliance portion 31 along an axial direction 30, the compliance portion 31 is depressed within an acceptance portion 32 of the outer tube hub 15 via compression movement of the spring 29 to a compressed position (not shown). The movement of the compliance portion 31 allows for ease of connection of the rigid sheath 11 to the outer tube 10. When pressure is removed from the compliance portion 31 and the rigid sheath 11 is not attached, the compliance portion 31 returns to its original position (i.e., uncompressed position). In the uncompressed position, the compliance portion 31 is disposed on an exterior side 33 of the acceptance portion 32 and the spring 29 is uncompressed. When pressure is removed from the compliance portion 31 and the rigid sheath 11 is attached, the compliance structure 31 is in a semi-compressed position such that a portion of the compliance structure 31 remains within the acceptance portion 32, as illustrated in FIG. 5C.

In another exemplary embodiment, the spring 29 can be disposed on the exterior of the outer tube hub 15.

FIGS. 4A-C illustrate perspective views of the inner tube 9 (FIG. 4A) removed from being disposed within the outer tube 10 (FIG. 4B), and the rigid sheath 11 (FIG. 4C)

removed from being disposed around the outer tube 10. The inner tube 9 includes at least one flexible portion 34 and a rigid portion 36. The rigid portion 36 may include at least a portion of the inner tube 9 including the cutting surface 26 at the first end 24 of the inner tube and may also include a portion of the inner tube 9 near the second end 14 of the inner tube 9. The circumferential flexible portion 34 of the inner tube 9 is located near the first end 24 of the inner tube 9 and extends for a distance along the length of the inner tube 9, as illustrated in FIG. 4A. However, the invention is not limited to the configuration of the exemplary embodiment of FIG. 4A. The flexible portion 34 of the inner tube 9 can be located along any portion or the entire length of the inner tube 9. Additionally, the flexible portion 34 of the inner tube 9 can be located at multiple, different locations along the inner tube 9.

The outer tube includes at least one flexible portion 35 and the rigid portion 37. The rigid portion 37 may include at least a portion of the outer tube 10 including the cutting window 27 at the first end 25 of the outer tube and may also include a portion of the outer tube 10 near the second end 17 of the outer tube 10. The circumferential flexible portion 35 of the outer tube 10 is located near the first end 25 of the outer tube 10 and extends for a distance along the length of the outer tube 10, as shown in FIG. 4B. However, the invention is not limited to the configuration of the exemplary embodiment of FIG. 4B. The flexible portion 35 of the outer tube 10 can be located along any portion or the entire length of the outer tube 10. Additionally, the flexible portion 35 of the outer tube 10 can be located at multiple, different locations along the outer tube 10.

The flexible portion 35 of the outer tube 10 can encompass a greater portion of the outer tube 10 than the flexible portion 34 of the inner tube 9 or, in the alternative, the flexible portion 34 of the inner tube 9 can encompass a greater portion of the inner tube 9 than the flexible portion 35 of the outer tube 10. In the illustrated embodiment, the flexible portion 35 of the outer tube 10 starts at a position close to the cutting window 27 and extends for a distance, and the flexible portion 34 of the inner tube 9 starts at a position close to the cutting surface 26 and extends for a distance.

The flexible portions 34, 35 are radially, symmetrically bendable about a longitudinal axis 40 of the main unit 21 (FIGS. 3 and 7). That is, the flexible portions 34, 35 can be bend in any direction (up, down, left, right, and all directions in between). However, in one embodiment, for example, the flexible portions 34, 35 assume a substantially straight orientation when the main unit 21 is not inserted into the rigid sheath 11 (FIG. 7). In accordance with some embodiments, the flexible portions 34, 35 with the rigid portions 36, 37 can be formed in a one- or two-piece configuration. However, the flexible portions 34, 35 are not limited to these configurations and other configurations of the flexible portions 34, 35 are possible.

In the one-piece configuration, the inner and outer tubes 9, 10 are formed of a rigid material. The flexible portions 34, 35 are formed on the inner and outer tubes 9, 10 by laser cutting pieces of the rigid material of the tubes 9, 10 to form openings therein. The tubes 9, 10 including the openings are then wrapped with a layer of pliable material in order hold the inner and outer tubes, respectively, together. One such example of flexible portions can be found in U.S. Pat. No. 5,707,350, the disclosure of which is incorporated by reference in its entirety.

Figure 11:
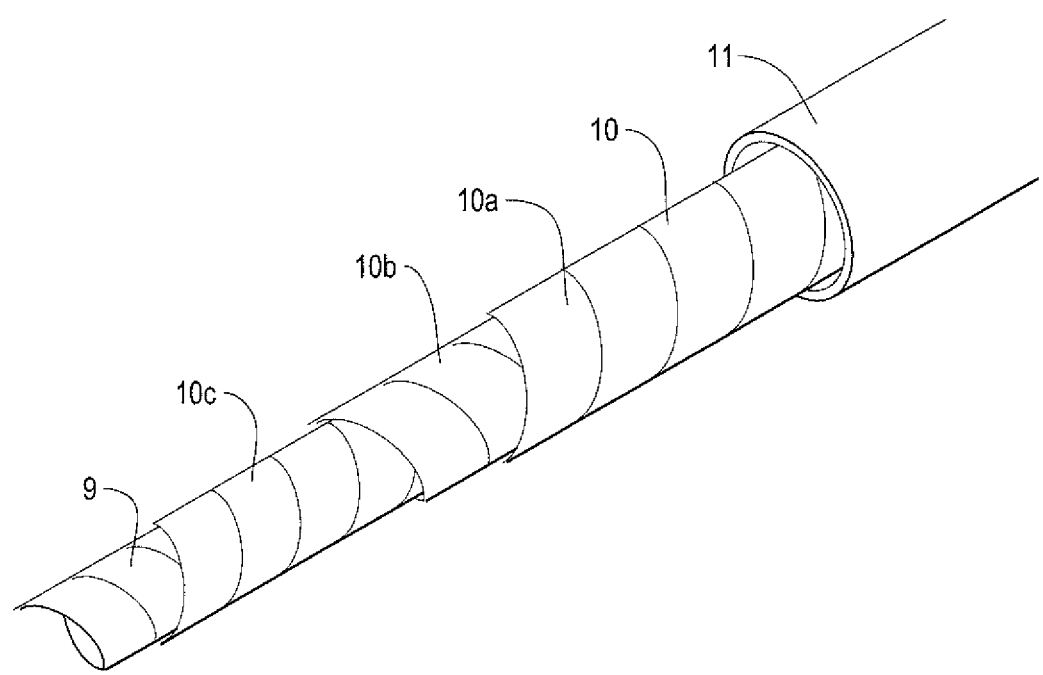
FIG. 11 is an elongated, perspective view of the inner and outer tubes of FIG. 2.

In the two-piece configuration, the rigid portions of the inner and outer tubes 9, 10 are formed of a rigid material. The flexible portions 34, 35 are formed separately from the rigid portions of the inner and outer tubes 9, 10. First, a first thin strip of metal is formed into a coil. Next, a second thin strip of metal is formed into a coil around the first thin strip of metal. The second thin strip of metal is coiled around the first thin strip of metal in a direction opposite that of the first thin strip of metal. Depending on the thickness required of the flexible portions 34, 35, a third thin strip of metal can be formed into a coil around the first and second thin strips of metal. The third thin strip of metal is coiled around the first and second thin strips of metal in a direction opposite that of the second thin strip of metal. Once the flexible portions are formed, the rigid portions of the inner and outer tubes can be attached to the flexible portion, for example, by spot welding. One such example of flexible portions can be found in U.S. Pat. No. 4,646,738, the disclosure of which is incorporated by reference in its entirety. FIG. 11 illustrates the configuration of the exemplary embodiment. In this two-piece configuration, the first thin strip 10*a*, second thin strip 10*b* and third thin strip 10*c* make up the flexible portion 35 of the outer tube 10. The inner tube 9 can be formed in the same manner as the outer tube so as to have a first thin strip, second thin strip and third thin strip (not shown) but could be formed from less strips such as one thin strip or from more strips.

As illustrated in FIGS. 5A-C, a first connector portion 38 is fixed to the outer tube 10, closer to the second end 17 of the outer tube 10 than the flexible portion 35, and a second connector portion 39 is formed on a second end 42 of the rigid sheath 11. In the exemplary embodiment, the second connector portion 39 includes a plurality of individually selectable engagement members 39*a*-39*d* (FIG. 10) and the first connector portion 38 is an engaging member that can be selectively engaged in one of the engagement members 39*a*-39*d*. The engaging member can be a protruding key and the engagement members 39*a*-*d* can be a plurality of slots; however, the invention is not limited to a key and slot arrangement and can employ any configuration of an engaging member and engagement members while still allowing for the selective and rotationally adjustable coupling of the rigid sheath 11 to the main unit 21. The engagement of the engaging member 38 with one of the engagement members 39*a*-*d* detachably couples the rigid sheath 11 to the main unit 21 such that the outer tube 10 cannot rotate relative to the rigid sheath 11. When the engaging member 38 is not engaged with one of the engagement members 39*a*-*d*, the main unit 21 can be completely removed from the rigid sheath 11.

The placement of the first connector portion 38 and second connector portion 39 is not limited to the embodiment described above and illustrated herein. The first connector portion can include either a plurality of individually selectable engagement members or an engaging member. Additionally, the first connector portion 38 can be located anywhere on the main unit 21 or rigid sheath 11 as long as the rigid sheath 11 is removably attachable to the main unit 21. The second connector portion 39 can include the other of either a plurality of individually selectable engagement members or an engaging member. Additionally, the second connector portion can be located anywhere on the main unit 21 or rigid sheath 11 as long as the rigid sheath 11 is removably attachable to the main unit 21.

In order to assemble the surgical tool, the inner tube 9 is inserted into the fluid passage 20 of the outer tube 10 via the second end 17 of the outer tube 10 until the cutting surface 26 of the inner tube 9 is aligned with the cutting window 27 of the outer tube 10 (FIG. 7). FIG. 7 illustrates the substantially straight orientation of the inner and outer tubes 9, 10 when not disposed in the rigid sheath 11. However, as discussed previously, it should be appreciated that the inner and outer tubes will be pre-assembled prior to delivery to the customer. Thus, a customer will most likely not be inserting the inner tube into the outer tube. Instead, the customer will merely be attaching and detaching the rigid sheath from the main unit.

FIGS. 5A-C illustrate the connection between the engaging member 38 and one of the engagement members 39. The main unit 21 is inserted into the an opening 44 of the second end 42 of the rigid sheath 11 (FIG. 5A) until the cutting window 27 with exposed cutting surface 26 extends beyond an opening 43 of the first end 41 of the rigid sheath 11 (FIGS. 4 and 6A-D). The engaging member 38 extends through an opening 46 of the one engagement member 39 for a distance until a base 47 of the rigid sheath 11 contacts the compliance portion 31. Pressure is then applied to the rigid sheath 11 forcing movement of the compliance portion 31 in an axial direction 30 so that the compliance portion 31 is depressed within the acceptance portion 32 of the outer tube hub 15 via compression movement of the spring 29 to the compressed position (FIG. 5B). In this compressed position, the engaging member 38 contacts or nearly contacts the top 48 of the engagement member 39. The rigid sheath 11 is then rotated in the circumferential direction for a distance before the compressing force is released thus allowing the compliance portion 31 to move to a semi-compressed position and the engaging member 38 to contact the lock portion 49 of the engagement member 39. In this position, the rigid sheath 11 is temporarily fixed/coupled to the outer tube 10 of the main unit 21 (FIG. 5C).

The rigid sheath 11 can be decoupled from the outer tube 10 by applying pressure to the rigid sheath 11 thus forcing the compliance portion 31 to become depressed within the acceptance portion 32 of the outer tube hub 15 via compression movement of the spring 29 to the compressed position (not shown). In this compressed position, the engaging member 38 contacts or nearly contacts the top 48 of the engagement member 39. The rigid sheath 11 is then rotated in the reverse circumferential direction (reverse of the direction used to couple of the rigid sheath 11 to the outer tube 10) before the compressing force is released thus allowing the compliance portion 31 to return to the uncompressed position and the engaging member 38 to be located in the opening 46 of the engagement member. The main unit 21 can then be completely removed from the rigid sheath 11.

Figure 10:
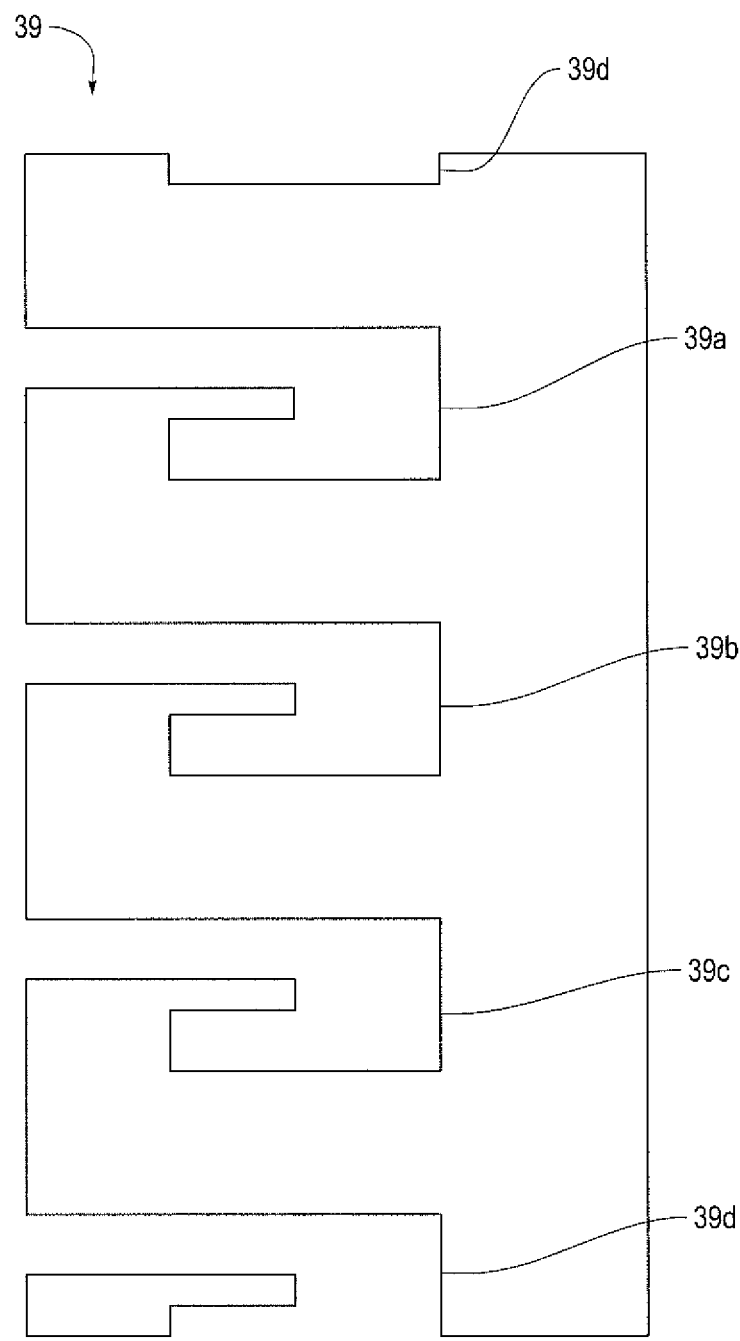
FIG. 10 is a simplified, top view of the engagement portions having been cut down the longitudinal axis and laid open, according to an exemplary embodiment.

In the exemplary embodiment of FIG. 10, the second connector portion 39 includes four engagement members 39a-d. The four engagement members 39 are formed on the rigid sheath 11 in intervals of 90° about the longitudinal axis 40 of the surgical tool. However, the second connector portion is not limited to this configuration. At a minimum, the second connector portion 39 should include at least one engagement member 39 but is not limited to four engagement members 39. The adjustable connection between engaging member 38 and a single or plurality of engagement members 39 allows for the orientation of the cutting window 27 relative to the longitudinal axis 40 of the rigid sheath 11 to be radially adjusted.

Figure 6A:
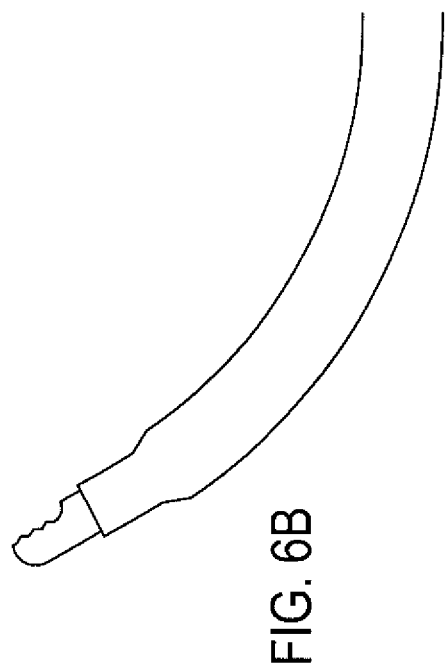
FIGS. 6A-D are simplified, side views of a portion of the surgical tool of FIG. 2.
Figure 6B:
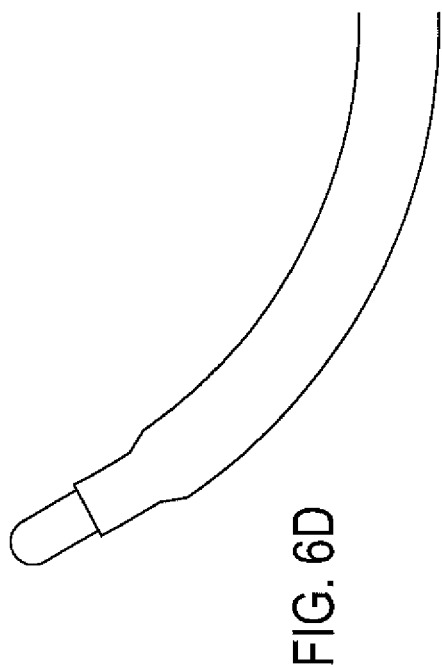
Figure 6C:
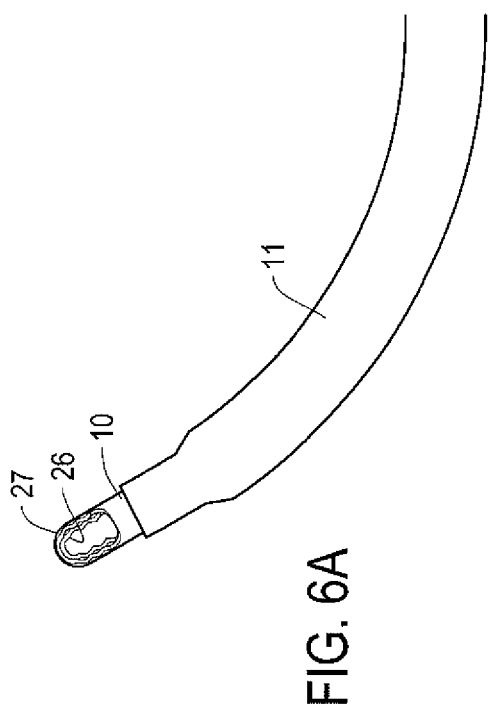
Figure 6D:
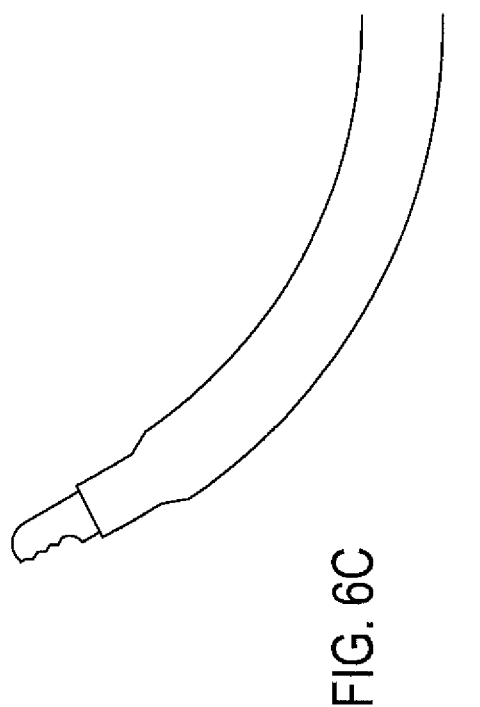

FIGS. 6A-D illustrate the adjustment of the orientation of the cutting window 27 relative to the longitudinal axis 40 of the rigid sheath 11 by engagement of the engaging member 38 with each of the four engagement members 39a-d of the exemplary embodiment. FIG. 6A illustrates the engagement of the engaging member 38 with the first engagement member 39a so as to orient the cutting window 27 in an outwardly facing position. FIG. 6B illustrates the engagement of the engaging member 38 with the second engagement member 39b so as to orient the cutting window 27 in an upwardly facing position. FIG. 6C illustrates the engagement of the engaging member 38 with the third engagement member 39c so as to orient the cutting window 27 in a downwardly facing position. FIG. 6D illustrates the engagement of the engaging member 38 with the fourth engagement member 39d so as to orient the cutting window 27 in a backwardly facing position.

Figure 8:
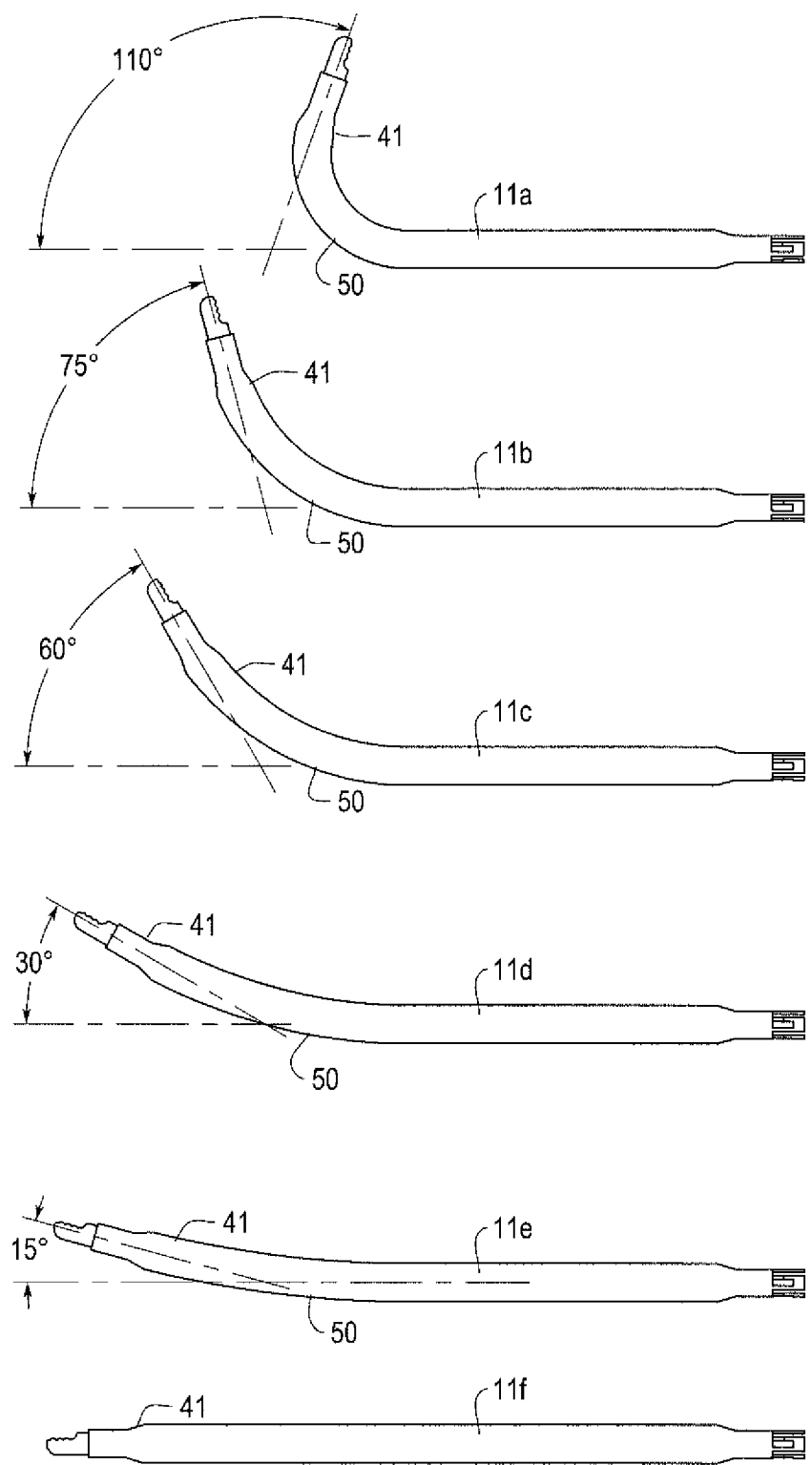
FIG. 8 is a simplified, side view of a set (or kit) of sheaths having different curved portions that can be used with the inner and outer tubes of FIG. 7, for example.

FIG. 8 illustrates an exemplary embodiment of a set or kit of rigid sheaths 11a-f having different shapes. For example, rigid sheath 11f is straight along its entire length and thus orients the flexible portions 34, 35 of the inner and outer tubes 9, 10, respectively, to have a straight orientation. Each of rigid sheaths 11a-e include a curved portion 50 at least near the first end 41 of the rigid sheath. An angle of the curved portion can be one of 15°, 30°, 40° (not shown), 60°, 75°, and 110°, but is not limited to these angles. Thus, the rigid sheath orients the flexible portions 34, 35 of the inner and outer tubes 9, 10, respectively, to the angle of the curved portion 50 of the rigid sheath. The set of rigid sheaths can be supplied with a single main unit 21. During surgery, the surgeon can selectively use the main unit with one, more than one, or all of the rigid sheaths.

Figure 9A:
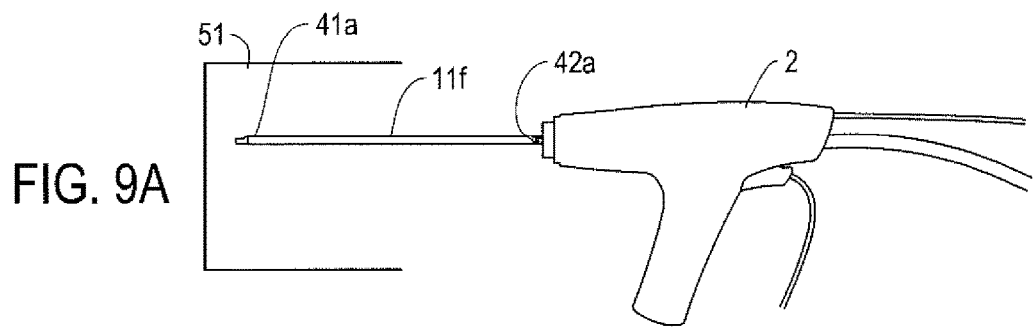
FIGS. 9A-E are side views of the surgical tool of FIG. 2 during a surgical procedure in which it is deployed in the passage of a patient.
Figure 9B:
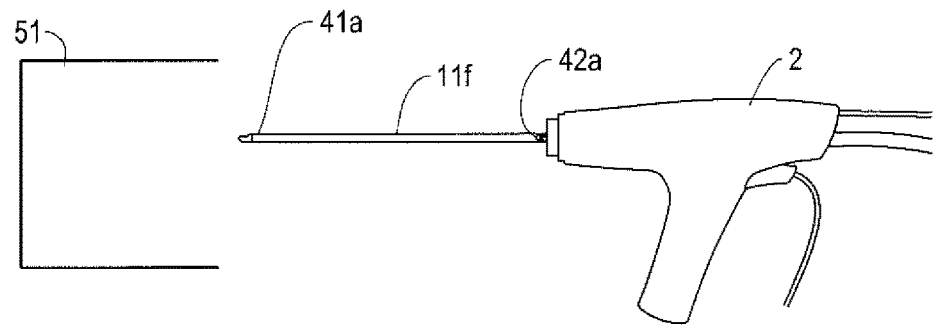
Figure 9C:
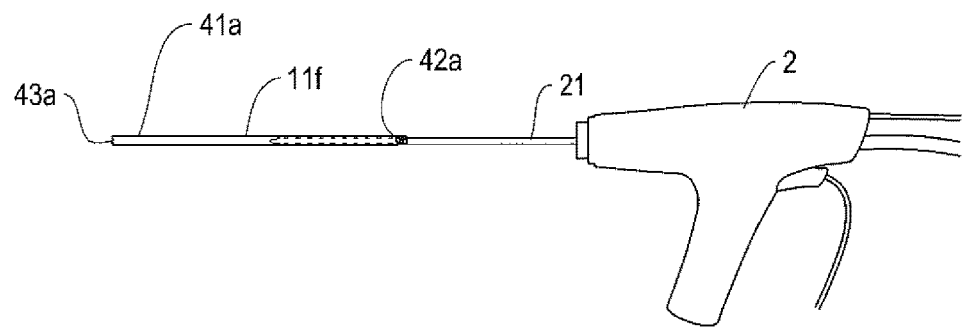
Figure 9D:
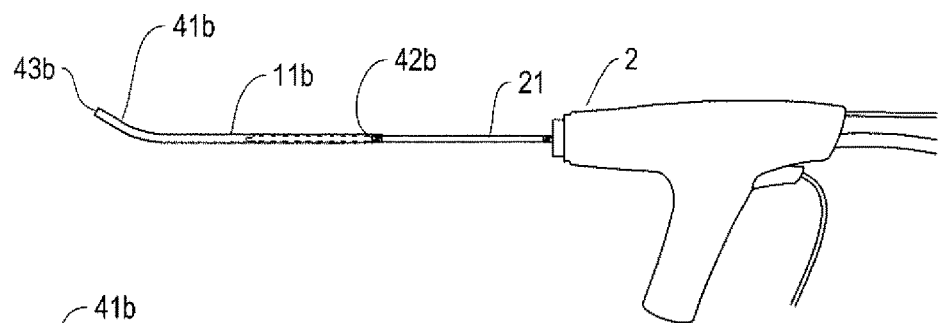
Figure 9E:
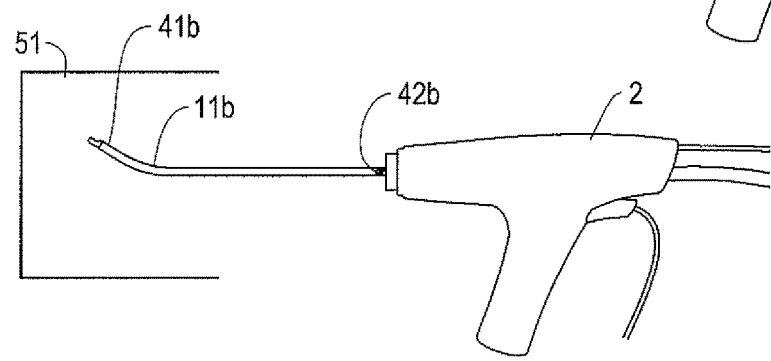

The surgical tool 8 of the above described embodiments can be used to perform surgical procedures. As illustrated in FIG. 9A, the surgical tool including the main unit 21 and a first rigid sheath 11f is inserted into a passage 51 of a patient so as to perform surgery using the surgical tool 8. The surgical tool is then removed from the passage of the patient 51 (FIG. 9B). The first rigid sheath 11f is completely removed from the main unit 21, as described above (FIG. 9C), and a second rigid sheath 11b is attached to the main unit 21 (FIG. 9D). The second rigid sheath 11b has a different shape from the first rigid sheath 11a. The surgical tool including the main unit 21 and second rigid sheath 11b is inserted into the passage of the patient 51 so as to perform surgery using the surgical tool 8 having the main unit 21 coupled to the second rigid sheath 11b (FIG. 9E). In addition to replacing one rigid sheath with another, the surgeon can decouple the rigid sheath from the main unit 21, change the orientation of the cutting window to the same rigid sheath (by rotating the rigid sheath relative to the main unit), and then recouple the main unit 21 to the same rigid sheath.

As noted above, a surgical tool kit can be provided to the surgeon. The surgical tool kit provides a plurality of differently shaped sheaths (i.e., sheaths with curved portions of varying angles), as discussed above, and a single main unit 21. The surgical tool kit allows for the continued use of the single main unit 21 and the interchangeability of the sheaths so as to orient the inner and outer tubes 9, 10 of the main unit 21 to specific angles without having to completely change the main unit 21. The surgical tool kit provides at least a first rigid sheath 11a having a first end 41a and a second end 42a. The first rigid sheath 11a can be removably attached to the main unit 21 such that the cutting window extends beyond an opening 43a of the first end 41a of the first rigid sheath 11a, as disclosed above with respect to the coupling of the rigid sheath 11 to the main unit 21. The first rigid sheath 11a can be exchanged for the second rigid sheath 11b. The second rigid sheath 11b is then removably attached to the main unit 21 such that the cutting window extends beyond an opening 43b of the first end 41b of the second rigid sheath 11b, as disclosed above with respect to the coupling of the rigid sheath 11 to the main unit 21. Various kit embodiments may include sheaths having curved portions of any angle, as well as providing any number of sheath options to choose from.

The illustrated exemplary embodiments of the surgical tool as set forth above are intended to be illustrative and not limiting. Various changes may be made without departing from the spirit and scope of the invention.

What is claimed is:

1. A surgical tool comprising:
   a main unit including:
      an inner tube having a first end and a second end, the inner tube including a cutting surface at the first end and a flexible portion located between the first end and the second end; and
      an outer tube having a first end and a second end, the outer tube including a cutting window at the first end and a flexible portion located between the first end and the second end, the inner tube received within the outer tube so as to align the cutting surface of the inner tube with the cutting window of the outer tube;
   a rigid sheath having a first end and a second end, the rigid sheath removably receives the main unit such that the cutting window extends beyond an opening of the first end of the rigid sheath; and
   a connector including:
      a first connector located directly on the outer tube adjacent to the second end of the outer tube such that the flexible portion of the outer tube is located between the first connector and the first end of the outer tube; and
      a second connector that is located at the second end of the rigid sheath and has an outer diameter equal to or smaller than a central portion of the rigid sheath between the first end and the second end of the rigid sheath, the first connector when connected to the second connector detachably couples the rigid sheath to the outer tube,
   wherein the main unit is configured to be completely removable from the rigid sheath when the first and second connectors are uncoupled from each other.

2. The surgical tool of claim 1, wherein the rigid sheath is constrained against rotation relative to the outer tube when the first and second connectors are coupled to each other.

3. The surgical tool of claim 1, further including a first tapered portion of the rigid sheath extending from the first end of the rigid sheath for a first tapered distance along the rigid sheath, the first tapered portion having a diameter smaller than a central portion of the rigid sheath.

4. The surgical tool of claim 3, further including a second tapered portion of the rigid sheath extending from the second end of the rigid sheath for a second tapered distance along the rigid sheath, the second tapered portion having a diameter smaller than the diameter of the central portion of the rigid sheath.

5. The surgical tool of claim 4, further including an untapered portion extending between the first tapered portion and the second tapered portion, the untapered portion having a larger diameter than the first and second tapered portions.

6. The surgical tool of claim 1, wherein the first and second connectors are adjustably connectable to each other such that an orientation of the cutting window relative to a longitudinal axis of the rigid sheath can be radially adjusted.

7. The surgical tool of claim 1, wherein the flexible portion of the inner tube and the flexible portion of the outer tube are radially, symmetrically bendable about a longitudinal, central axis of the surgical tool.

8. The surgical tool of claim 1, wherein the rigid sheath is straight along an entire length of the rigid sheath.

9. The surgical tool of claim 1, wherein the rigid sheath includes a curved portion at least near the first end of the rigid sheath.

10. The surgical tool of claim 9, wherein an angle of the curved portion is one of 15°, 30°, 40°, 60°, 75°, and 110°.

11. The surgical tool of claim 1, wherein the flexible portion of the inner tube is located at least near the first end of the inner tube, and the flexible portion of the outer tube is located at least near the first end of the outer tube.

12. The surgical tool of claim 1, wherein the outer tube of the main unit cannot rotate relative to the rigid sheath when the first and second connectors are coupled to each other.

13. The surgical tool of claim 1, wherein the cutting window extends through the opening located at the first end of the rigid sheath and the cutting window protrudes beyond the first end of the rigid sheath.

14. The surgical tool of claim 1, wherein:
   the first connector located on the outer tube adjacent to the second end of the outer tube is a protrusion; and
   the second connector located at the second end of the rigid sheath includes a plurality of slots that extend in a longitudinal direction of the rigid sheath and that pass entirely through a thickness of a wall defining the rigid sheath from an inner surface of the wall to an outer surface of the wall.

15. The surgical tool of claim 1, wherein the rigid sheath removably receives the main unit such that the first end of the rigid sheath is located between the first end of the outer tube and the flexible portion of the outer tube.

16. The surgical tool according to claim 1, wherein the first connector and the second connector are configured to be connected by moving the rigid sheath axially over the outer tube until one of the first connector and the second connector extends through an opening in the other of the first connector and the second connector, and then rotating the rigid sheath in a circumferential direction for a distance to connect the first connector and the second connector.

17. The surgical tool according to claim 1, wherein the first connector is directly fixed to the outer tube between the flexible portion and an outer tube hub disposed on the second end of the outer tube.

18. The surgical tool according to claim 1, wherein the second connector is disposed within a wall of a portion of the rigid sheath.

19. The surgical tool according to claim 1, wherein the first connector is disposed around only a portion of a circumference of the outer tube.

20. A surgical tool kit comprising:
   a main unit including:
      an inner tube having a first end and a second end, the inner tube including a cutting surface at the first end and a flexible portion located between the first end and the second end; and
      an outer tube having a first end and a second end, the outer tube including a cutting window at the first end and a flexible portion located between the first end and the second end, the inner tube received within the outer tube so as to align the cutting surface of the inner tube with the cutting window of the outer tube;
   a first rigid sheath having a first end and a second end, the first rigid sheath being configured to be removably attachable directly to the outer tube such that the cutting window extends through an opening located at the first end of the first rigid sheath and such that the cutting window protrudes beyond the first end of the first rigid sheath, the first rigid sheath including a connector that is located at the second end of the first rigid sheath and has an outer diameter equal to or smaller than a central portion of the first rigid sheath between the first end and the second end of the first rigid sheath; and at least one additional rigid sheath having a first end and a second end, the at least one additional rigid sheath being configured to be removably attachable directly to the outer tube instead of the first rigid sheath such that the cutting window extends through an opening located at the first end of the at least one additional rigid sheath and such that the cutting window protrudes beyond the first end of the at least one additional rigid sheath, wherein the at least one additional rigid sheath has a shape that is different from a shape of the first rigid sheath.

21. The surgical tool kit of claim 20, wherein each of the first rigid sheath and the at least one additional rigid sheath has a first tapered portion that extends from the first end of the rigid sheaths for a first tapered distance along the rigid sheaths, the first tapered portion having a diameter smaller than a diameter of a central portion of the rigid sheaths.

22. The surgical tool kit of claim 21, wherein each of the first rigid sheath and the at least one additional rigid sheath has a second tapered portion that extends from the second end of the rigid sheaths for a second tapered distance along the rigid sheaths, the second tapered portion having a diameter smaller than the diameter of the central portion of the rigid sheaths.

23. The surgical tool kit of claim 22, wherein an untapered portion of each of the first rigid sheath and the at least one additional rigid sheath extends between the first tapered portion and the second tapered portion, the untapered portion having a larger diameter than the first and second tapered portions.

24. The surgical tool kit of claim 20, wherein the first rigid sheath is straight and the at least one additional rigid sheath has a curved portion at least near the first end thereof.

25. The surgical tool kit of claim 24, further comprising:
 a plurality of the additional rigid sheaths, each having a differently-curved curved portion.

26. The surgical tool kit of claim 24, wherein an angle of the curved portion is one of 15°, 30°, 40°, 60°, 75°, and 110°.

27. The surgical tool kit of claim 20, further comprising:
 a plurality of the additional rigid sheaths, each having a shape that is different from each other and from the shape of the first rigid sheath.

28. The surgical tool kit of claim 20, wherein the first rigid sheath and the at least one additional rigid sheath each removably receive the main unit such that the first end of the first rigid sheath and the first end of the at least one additional rigid sheath is located between the first end of the outer tube and the flexible portion of the outer tube.

* * * * *